United States Patent
Ziv-Ari et al.

(10) Patent No.: US 12,329,575 B2
(45) Date of Patent: Jun. 17, 2025

(54) CONTROLLING AND VISUALIZING ROTATION AND DEFLECTION OF A 4D ULTRASOUND CATHETER HAVING MULTIPLE SHAFTS

(71) Applicant: Biosense Webster (Israel) Ltd., Yokneam (IL)

(72) Inventors: Morris Ziv-Ari, Atlit (IL); Yochai Parchak, Raanana (IL); Avigdor Rosenberg, Kiryat Tivon (IL)

(73) Assignee: Biosense Webster (Israel) Ltd., Yokneam (IL)

( * ) Notice: Subject to any disclaimer, the term of this patent is extended or adjusted under 35 U.S.C. 154(b) by 395 days.

(21) Appl. No.: 17/572,314

(22) Filed: Jan. 10, 2022

(65) Prior Publication Data

US 2023/0218272 A1    Jul. 13, 2023

(51) Int. Cl.
| | |
|---|---|
| A61B 8/00 | (2006.01) |
| A61B 8/08 | (2006.01) |
| A61B 8/12 | (2006.01) |

(52) U.S. Cl.
CPC ............ *A61B 8/445* (2013.01); *A61B 8/0883* (2013.01); *A61B 8/12* (2013.01); *A61B 8/4466* (2013.01); *A61B 8/4494* (2013.01); *A61B 8/461* (2013.01)

(58) Field of Classification Search
CPC ......... A61B 8/445; A61B 8/0883; A61B 8/12; A61B 8/446
See application file for complete search history.

(56) References Cited

U.S. PATENT DOCUMENTS

| | | | |
|---|---|---|---|
| 6,248,074 B1 | 6/2001 | Ohno et al. | |
| 6,332,089 B1 | 12/2001 | Acker et al. | |
| 6,618,612 B1 | 9/2003 | Acker et al. | |
| 7,798,966 B2 | 9/2010 | Kawashima et al. | |
| 2002/0065455 A1 | 5/2002 | Ben-Haim et al. | |
| 2003/0120150 A1 | 6/2003 | Govari | |
| 2004/0068178 A1 | 4/2004 | Govari | |
| 2004/0147837 A1* | 7/2004 | Macaulay | A61B 8/0833 600/117 |
| 2012/0136626 A1* | 5/2012 | Mucha | A61B 34/20 702/150 |
| 2013/0150739 A1* | 6/2013 | Amit | A61B 18/1492 604/528 |

(Continued)

OTHER PUBLICATIONS

International Search Report mailed Mar. 24, 2023 from corresponding PCT Patent Application No. PCT/IB2022/062031.

*Primary Examiner* — Joseph M Santos Rodriguez
*Assistant Examiner* — Tommy T Ly
(74) *Attorney, Agent, or Firm* — Smith, Gambrell & Russell, LLP; Michael J. Riesen

(57) ABSTRACT

A catheter includes: a shaft for insertion into an organ of a patient, and first and second position sensors. The shaft includes: (a) an inner shaft, which is configured to be deflected relative to an axis of the shaft, and (b) an outer shaft, which is coupled to a distal tip of the catheter and is configured to be: (i) coaxially disposed around the inner shaft, (ii) deflected together with the inner shaft, and (iii) rotated about the axis relative to the inner shaft. The first position sensor is coupled to the distal tip and is configured to produce a first signal, and the second position sensor is coupled to the inner shaft, and is configured to produce a second signal.

21 Claims, 4 Drawing Sheets

(56) References Cited

U.S. PATENT DOCUMENTS

| | | |
|---|---|---|
| 2015/0157408 A1* | 6/2015 | Viswanathan ........... A61B 5/06 600/424 |
| 2017/0086786 A1 | 3/2017 | Moore et al. |
| 2017/0120080 A1* | 5/2017 | Phillips .................. A61B 34/25 |
| 2018/0172420 A1 | 6/2018 | Hein et al. |
| 2018/0279994 A1 | 10/2018 | Schaer et al. |
| 2020/0061340 A1* | 2/2020 | Mixter ................. A61B 8/4466 |
| 2020/0102389 A1 | 4/2020 | Fischer et al. |
| 2020/0315741 A1 | 10/2020 | Gliner et al. |
| 2021/0275255 A1 | 9/2021 | Govari et al. |
| 2022/0304660 A1* | 9/2022 | Loype ..................... A61B 8/54 |

\* cited by examiner

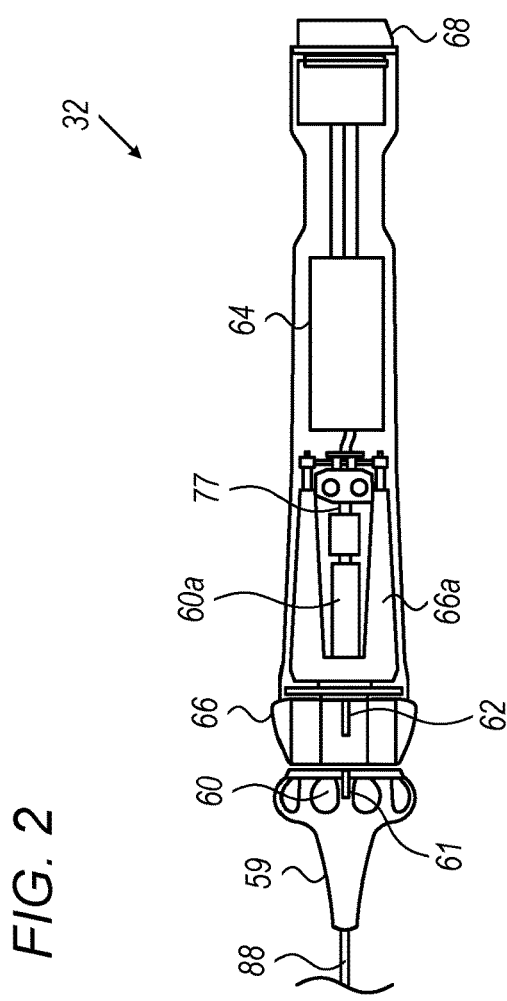
FIG. 2
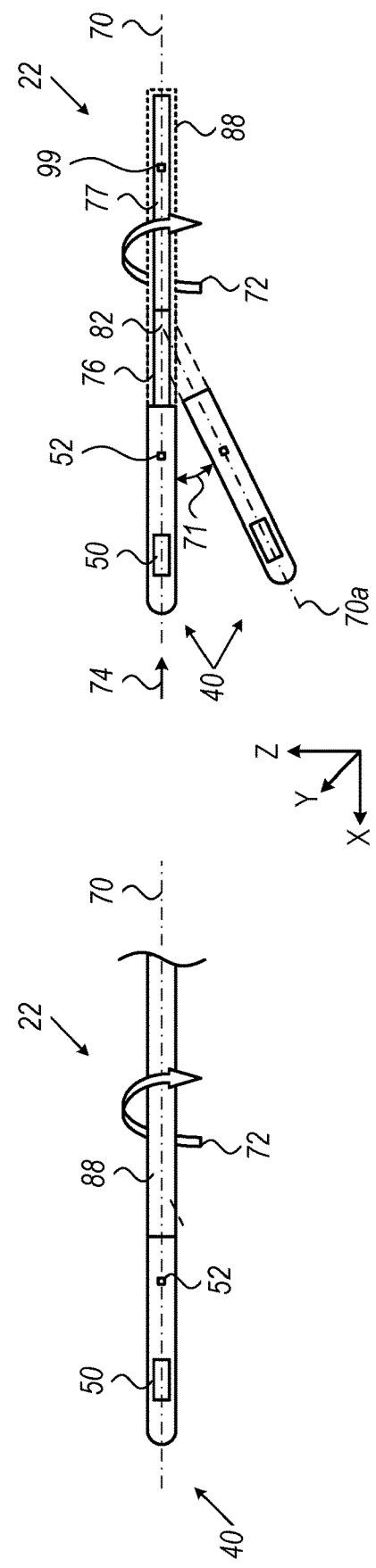
FIG. 3A
FIG. 3B

CONTROLLING AND VISUALIZING ROTATION AND DEFLECTION OF A 4D ULTRASOUND CATHETER HAVING MULTIPLE SHAFTS

FIELD OF THE DISCLOSURE

The present disclosure relates generally to medical imaging, and particularly to methods and systems for controlling and manipulating a four-dimensional (4D) ultrasound catheter.

BACKGROUND OF THE DISCLOSURE

Various techniques for controlling manipulation of catheters in an organ of a patient have been published.

For example, U.S. Patent Application Publication 2021/0275255 describes a system that includes a medical instrument, a position sensor, and a processor. The medical instrument includes a handle and a head, the head being configured for insertion into an organ of a patient and having a feature that is rotationally-asymmetric about a longitudinal axis of the medical instrument. The position sensor is disposed on the head and is configured to generate signals in response to an externally-applied magnetic field. The processor is configured to receive the signals generated by the position sensor on the head, and to estimate, based on the received signals, a roll angle of the rotationally-asymmetric feature of the head.

The present disclosure will be more fully understood from the following detailed description of the examples thereof, taken together with the drawings in which:

BRIEF DESCRIPTION OF THE DRAWINGS

FIG. 2 is a schematic, pictorial illustration of a handle of a catheter of the ultrasound imaging system, in accordance with examples of the present disclosure;

FIGS. 3A and 3B are schematic, pictorial illustrations of a shaft of the catheter of the ultrasound imaging system, in accordance with examples of the present disclosure;

DETAILED DESCRIPTION OF EXAMPLES

Overview

Figure 1:
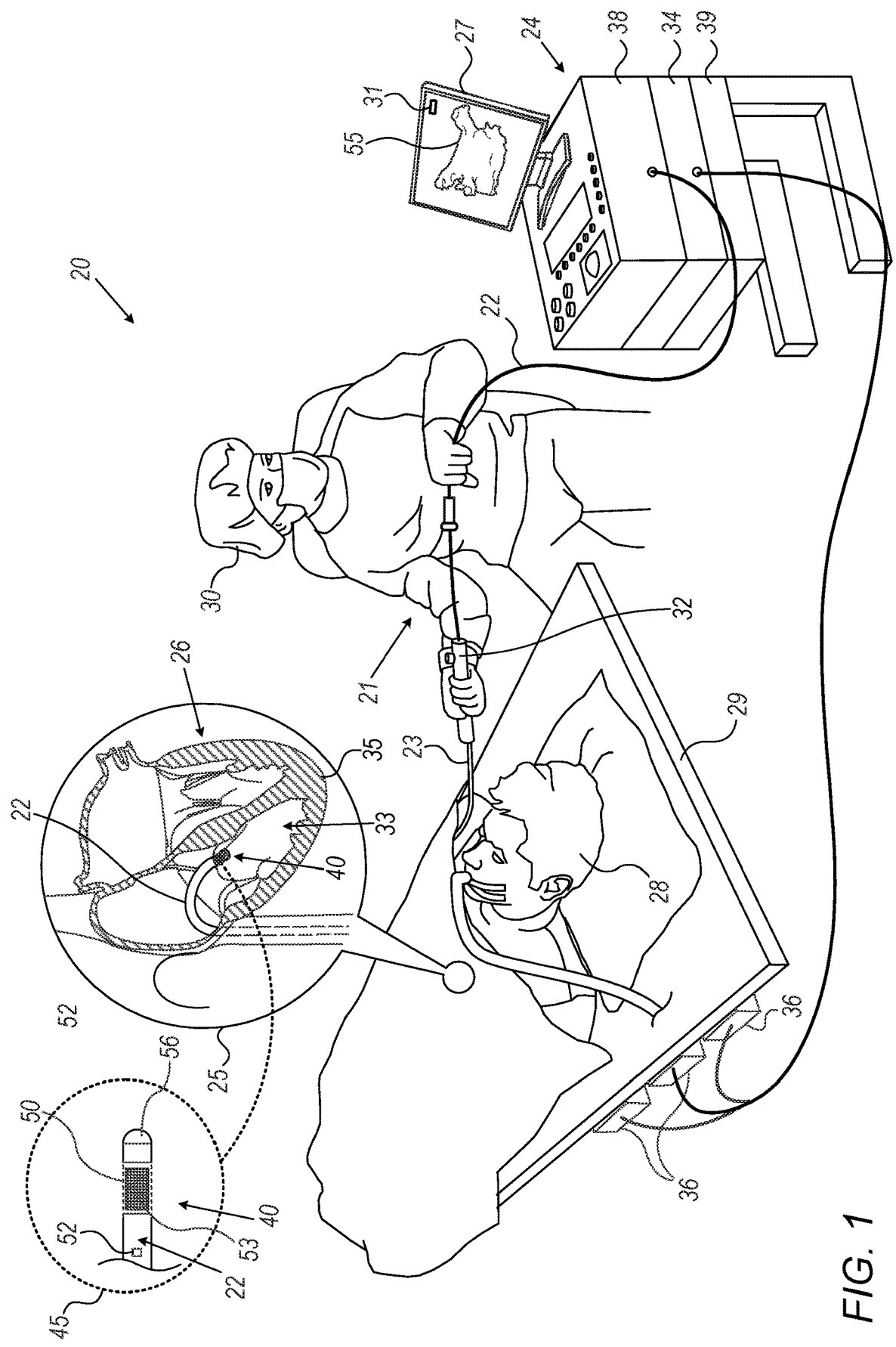
FIG. 1 is a schematic, pictorial illustration of a catheter-based ultrasound imaging system, in accordance with an example of the present disclosure.

Ultrasound imaging may be carried out in-vivo by inserting a four-dimensional (4D) ultrasound (US) catheter into an organ in question. For example, 4D Intra-Cardiac Echocardiography (ICE) imaging may provide visualizing of an ablation catheter within a three-dimensional (3D) space of a cavity of a patient heart. In the context of the present disclosure, the term 4D refers to imaging of a 3D space over time (which is the fourth dimension), and producing a video clip of 3D US images of the cavity in question.

Examples of the present disclosure that are described hereinbelow provide improved techniques for controlling the manipulation of a 4D US catheter having at least two shafts. For example, an inner shaft configured to be deflected and an outer shaft, which is configured to be rotated relative to the inner shaft, and is coupled to a distal tip of the 4D US catheter that performs the ICE imaging.

In some examples, a (4D) ultrasound catheter comprises the inner and outer shaft described above, and the distal end of the catheter, which is coupled to the outer shaft, comprises one or more ultrasound transducers (UT), arranged in a two-dimensional (2D) array and configured to apply US waves to an organ in question (e.g., heart cavity), and to produce, based on US waves returned (e.g., reflected) from the cavity in question, one or more US signals indicative of the shape and morphology of the cavity and surrounding tissue in question.

The position and orientation of the distal tip of a 4D US catheter that combines a deflected shaft and a rotated shaft, has six degrees of freedom (DOF). In principle, it is possible to couple to the distal tip, a triple-axis magnetic-based position sensor, also referred to herein as a triple-axis sensor (TAS), of a position tracking system. The TAS may be used for tracking the position and orientation of the distal tip in the 6 DOF. However, the TAS comprises at least three coils that are produced on a circuit board or using any other suitable arrangement, and capture a substantial real estate of the distal tip. The size of the TAS forces two undesired design options: (a) increased diameter of the distal tip, or (b) limiting the number of components in the distal tip. Both options are limiting the functionality and applicability of the distal tip and the respective catheter.

In some examples, a 4D ICE system comprises a 4D ICE catheter having: (a) the inner shaft, which is configured to be deflected relative to a longitudinal axis of the catheter, (b) the outer shaft, which is coupled to the distal tip and is configured to be: (i) coaxially disposed around the inner shaft, (ii) deflected together with the inner shaft, and (iii) rotated about the longitudinal axis relative to the inner shaft.

In some examples, the 4D ICE catheter comprises a first position sensor, in the present example a dual-axis sensor (DAS) that captures a significantly smaller real estate than that of the TAS, is coupled to the distal tip and is configured to produce a first signal.

In some examples, the 4D ICE catheter comprises a second position sensor, in the present example a DAS or a single-axis sensor (SAS), which is coupled to the inner shaft, and is configured to produce a second signal.

In some examples, the 4D ICE catheter comprises a handle, which is configured to manipulate the distal tip by controlling: (i) the deflection of the inner shaft, and (ii) the rotation of the outer shaft. In the present example, the deflection and rotation control are implemented using respective deflection knob and rotation knob. During the procedure, a user of the catheter (e.g., a physician) rotates the knobs about a longitudinal axis of the handle (which is typically parallel to the longitudinal axis of the catheter) for controlling deflection and rotation of the distal tip. Note that the knobs have respective markers whose positions are indicative of the deflection angle and rotation angle applied to the distal tip through the inner and outer shafts, respectively. However, in case the user wants to know the current status of the deflection and rotation angles, he or she must, undesirably, direct the gaze away from a main display of the system, and look at the markers of the handle.

In some examples, the 4D ICE system comprises a processor, which is configured, based on the first and second signals, to display to the user (e.g., on the main display), one or more parameter indicative of at least one of: (i) the rotation angle of the inner shaft and/or of the distal tip, (ii) the deflection angle of the outer shaft and/or of the distal tip, and (iii) the position and orientation of the distal tip within the cavity of the heart.

Figure 4:
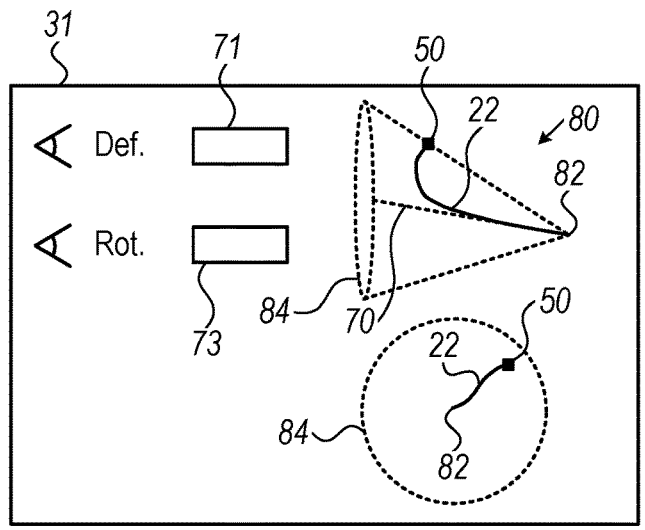
FIG. 4 is a schematic, pictorial illustration of a frame for presenting one or more parameters indicative of the amount of rotation and/or deflection of the shaft, in accordance with an example of the present disclosure.

In some examples, the processor is configured to display the parameters on the main display, using one or both of: a graphic representation, and a numeric representation of the parameters. Examples of the representation are shown in FIG. 4 of the detailed description.

The disclosed techniques improve the functionality and applicability of ultrasound-based 4D ICE catheters, by enabling: (i) reduced diameter of the distal tip, and/or (ii) increased functionality by reducing the size of the position sensor and allowing introduction of additional components into the distal tip. Moreover, the disclosed techniques improve the quality of 4D ICE procedures by displaying to the user, e.g., on the main display of the ICE system, all the information related to the manipulation and position tracking of the distal tip.

System Description

FIG. 1 is a schematic, pictorial illustration of a catheter-based ultrasound imaging system 20, in accordance with an example of the present disclosure.

Reference is now made to an inset 45. In some examples, system 20 comprises a catheter 21 having a distal end assembly, also referred to herein as a distal tip 40, which comprises one or more ultrasound transducers (UT) 53 that in the present example are arranged in a two-dimensional (2D) ultrasound array, also referred to herein as a 2D array 50 of the UT. Distal tip 40 further comprises a position sensor 52 coupled at a known position relative to 2D array 50. In the present example, position sensor 52 comprises a magnetic position sensor, but in other examples, position sensor 52 may comprise any other suitable type of position sensor.

In some examples, 2D array 50 is configured to apply ultrasound (US) waves to an organ, in the present example, a heart 26 of a patient 28, and to produce one or more US signals indicative of a surface topography and morphology of the respective tissue of heart 26.

In some examples, position sensor 52 is integrated with and is pre-registered with 2D array 50 of catheter 21.

In some examples, position sensor 52 is configured to produce one or more position signals indicative of one or more respective positions of distal tip 40 inside heart 26 of patient 28 lying on a surgical table 29, as will be described in more detail herein.

Reference is now made back to the general view of FIG. 1. In some examples, system 20 comprises a processor 39, which is configured, based on the position signals received from position sensor 52, to estimate the direction and the orientation of distal tip 40, and more specifically of 2D array 50 of the UT inside (a cavity of) heart 26. The position sensing techniques are described in more detail in FIGS. 3A and 3B below.

In some examples, based on the position signals received from position sensor 52 (and optionally additional position sensors coupled to the catheter), processor 39 is configured to produce an US image of heart tissue by registering between ultrasound images that were acquired using 2D array 50, in respective sections of the tissue of heart 26.

In some examples, distal tip 40 is fitted at the distal end of a shaft 22 of catheter 21, which is inserted through a sheath 23 into heart 26. Shaft 22 is described in more detail in FIGS. 3A and 3B below.

In some examples, the proximal end of catheter 21 is connected to a control console 24. In the example described herein, catheter 21 is used for ultrasound-based diagnostic procedures. In other examples, the catheter may be also used in therapeutic procedures, such as in electrical sensing and ablation of tissue in heart 26, using a tip electrode 56 shown in inset 45.

Reference is now made to an inset 25. In some examples, a physician 30 navigates distal tip 40 of catheter 21 to a target location in a cavity 33 of heart 26 by manipulating shaft 22 using a handle 32 located near the proximal end of catheter 21. Note that cavity 33 is surrounded by tissue 35 and by ostia of vasculature connected to cavity 33. In the example of FIG. 1, physician 30 navigates distal tip 40 into cavity 33, e.g., a right atrium of heart 26, and applies the UT of 2D array 50 for producing US images of the right atrium.

Reference is now made to insets 25 and 45. In some examples, physician 30 navigates 2D array 50 in cavity 33, and the navigation requires manipulation of shaft 22 for positioning distal tip 40 at required positions within the right atrium. In the present example, 2D array 50 comprises about 2048 UT 53 arranged in an array of about 64 columns and about 32 rows, and is configured to produce one or more US images of one or more respective sections of cavity 33 and tissue 35. Note that based on the position signals received from position sensor 52, the spatial coordinates of every pixel in the imaged section are known and registered for producing a full US image of the section in question. Note that the number of UT and the arrangement thereof in 2D array 50 is presented by way of example, and in other examples, 2D array 50 may comprise any other suitable number of UT 53 arranged in any similar or different suitable configuration.

In the context of the present disclosure and in the claims, the terms "about" or "approximately" for any numerical values or ranges indicate a suitable dimensional tolerance that allows the part or collection of components to function for its intended purpose as described herein.

Reference is now made back to the general view of FIG. 1. In some examples, control console 24 comprises processor 39, typically a general-purpose computer, with suitable front end and interface circuits 38 for receiving signals from catheter 21, as well as for, optionally, applying treatment via catheter 21 to tissue in heart 26 and for controlling the other components of system 20. Console 24 also comprises a driver circuit 34, configured to drive magnetic field generators 36.

In some examples, during the navigation of distal tip 40 in heart 26, console 24 receives position signals from position sensor 52 (and an additional position sensor described in FIG. 3B below) in response to magnetic fields from external field generators 36. In some examples, magnetic field generators 36 are placed at known positions external to patient 28, e.g., below table 29 upon which the patient is lying. The position signals are indicative of the position and direction of 2D array 50 in the coordinate system of a position tracking system, which is registered with the coordinate system of system 20.

The method of position sensing using external magnetic fields is implemented in various medical applications, for example, in the CARTO™ system, produced by Biosense Webster, and is described in detail in U.S. Pat. Nos. 6,618, 612 and 6,332,089, in PCT Patent Publication WO 96/05768, and in U.S. Patent Application Publications 2002/0065455, 2003/0120150, and 2004/0068178.

In some examples, processor 39 is configured to operate 2D array 50 for imaging cavity 33 (e.g., the right atrium) and/or surrounding tissue (e.g., tissue 35) of heart 26. The ultrasound waves are produced using the transducers of 2D array 50, which can both emit ultrasound waves, as well as detect the ultrasound echoes reflected back from the tissue. When used in an ultrasound scanner, the transducer sends out a beam of sound waves into the body. The sound waves are reflected back to the transducer by boundaries between tissues in the path of the beam (e.g. the boundary between fluid and soft tissue in the case of heart 26). When these echoes hit the transducer, they generate electrical signals that are sent to the ultrasound scanner. Using the speed of sound and the time of each echo's return, the scanner calculates the distance from the transducer to the tissue boundary. These distances are then used to generate 2D or 3D images of the tissues of heart 26.

In an example, processor 39 is configured to display at least a section of the imaged cavity 33 to physician 30 on a display 27, e.g., as an ultrasound image, referred to herein as an image 55, or using any other suitable presentation.

In some examples, physician 30 may use handle 32, which is configured to deflect and rotate shaft 22, for manipulating distal tip 40 to a desired position within cavity 33 of heart 26. The structure of handle 32 is described in detail in FIG. 2 below, and the structure of shaft 22 is described in FIGS. 3A and 3B below.

In some examples, processor 39 is configured to display to a user of system 20 (e.g., physician 30), one or more parameters indicative of the amount (e.g., angle) of deflection and/or rotation of shaft 22, which are indicative of the rotation and deflection angles of distal tip 40. In the present example, processor 39 is configured to display the one or more parameters within a frame 31 displayed on display 27. The one or more parameters may be displayed using a graphic representation, a numeric representation, or a combination thereof that is shown, by way of example, in FIG. 4 below. The parameters are related to the structure and features of handle 32 and shaft 22, which are described in detail in FIGS. 2, 3A and 3B below.

In some examples, processor 39 typically comprises a general-purpose computer, which is programmed in software to carry out the functions described herein. The software may be downloaded to the computer in electronic form, over a network, for example, or it may, alternatively or additionally, be provided and/or stored on non-transitory tangible media, such as magnetic, optical, or electronic memory.

The example configuration shown in FIG. 1 is chosen by way of example for the sake of conceptual clarity. The disclosed techniques may be applied, mutatis mutandis, using other components and settings of system 20. For example, system 20 may comprise additional components and are configured to perform catheterization procedures other than cardiac.

Controlling the Deflection and Rotation of a 4D Ultrasound Catheter

FIG. 2 is a schematic, pictorial illustration of handle 32 of catheter 21, in accordance with examples of the present disclosure. In some examples, handle 32 has a connector 68 configured to electrically connect between handle 32 and console 24 via a braid of wires threaded through shaft 22 (shown in FIG. 3B below), and a printed circuit board (PCB) 64, which is configured to exchange with processor 39 signals that are described in detail below. Another example implementation of a catheter handle and body in accordance with the present disclosure is described by International Publication Number WO 2020/102389 A1, entitled Medical Tool Positioning Devices, Systems, and Methods of Use and Manufacture, which is incorporated in its entirety herein.

In some examples, shaft 22 comprises an inner shaft 77, and an outer shaft 88, which are described in detail in FIGS. 3A and 3B below. In some examples, inner shaft 77 is configured to be deflected relative to an axis of shaft 22 and/or handle 32.

In some examples, outer shaft 88 is coupled to distal tip 40 of catheter 21 and is configured to be coaxially disposed around inner shaft 77. Outer shaft 88 is further configured to be deflected together with inner shaft 77, and to be rotated, about the axis of the shaft, relative to inner shaft 77. The rotation of outer shaft 88 together with distal tip 40, and the deflection of inner shaft 77 are described in detail in FIGS. 3A and 3B.

In some examples, handle 32 comprises a deflection assembly 66a, which is configured to deflect inner shaft 77 in a predefined range of rotation angles, e.g., between about −180° and +180° relative to the longitudinal axis of shaft 22. Handle 32 comprises a knob 66, also referred to herein as a deflection knob, which is configured to control deflection assembly 66a to carry out the deflection of inner shaft 77. Knob 66 comprises a deflection marker 62, whose position is indicative of the deflection angle of inner shaft 77 within the predefined range of rotation angles.

In some examples, handle 32 comprises a rotation assembly 60a, which is configured to rotate outer shaft 88 in a predefined range of rotation angles, e.g., between about −30° and +120° relative to the longitudinal axis of shaft 22. Handle 32 comprises a knob 60, also referred to herein as a rotation knob, which is configured to control rotation assembly 60a to carry out the rotation of outer shaft 88. Knob 66 comprises a deflection marker 61, whose position is indicative of the rotation angle of outer shaft 88 within the predefined range of rotation angles.

In some examples, handle 32 comprises a funnel-shaped distal end 59, which is configured to direct shaft 32 and distal tip 40 toward a target location in patient heart 26.

FIGS. 3A and 3B are schematic, pictorial illustrations of inner shaft 77 and outer shaft 88 of catheter 21, in accordance with examples of the present disclosure.

Reference is now made to FIG. 3A. In some examples, outer shaft 88 is coupled to distal tip 40, and is configured to be rotated, e.g., in a rotary direction 72, about an axis 70 that corresponds to a longitudinal axis of shaft 22. In the example of FIGS. 3A and 3B, axis 70 is parallel to an X-axis of an XYZ coordinate system.

In some examples, distal tip 40 is configured to be rotated together with outer shaft 88. In the present example, position sensor 52 comprises a dual-axis sensor (DAS), which is formed on a flexible circuit board (CB), also referred to herein as a flexible PCB. As described in FIG. 1 above, position sensor 52 is coupled at a known position relative to 2D array 50, and is configured to produce a signal (also referred to herein as a first signal) indicative of the position and orientation of 2D array 50. An example technique for implementing a multi-axis position sensor on a foldable PCB is described in U.S. Patent Application Publication 2017/0433072. In other examples, position sensor 52 may comprise a DAS that is implemented by integrating a plurality of (e.g., two) magnetic coils.

In alternative examples, position sensor 52 may comprise a triple-axis sensor (TAS) or a single-axis sensor (SAS). However, a TAS typically requires a relatively large real-estate of distal tip 40 (e.g., compared to a DAS), and a SAS may be insufficient for controlling the position and orientation of distal tip 40.

Reference is now made to FIG. 3A. In some examples, outer shaft 88 (shown in a broken frame) is coaxially disposed around inner shaft 77, which is configured to be deflected using deflection knob 66 and deflection assembly 66a of FIG. 2 above.

Reference is now made to FIG. 3B. In some examples, a position sensor 99 is coupled to inner shaft 77 and is configured to produce a signal (also referred to herein as a second signal) indicative of the position and/or orientation of inner shaft 77. In the present example, position sensor 99 comprises a magnetic position sensor, but in other examples, position sensor 99 may comprise any other suitable type of position sensor. In some examples, position sensor 99 comprises a dual-axis sensor (DAS), and in other example, position sensor 99 comprises a single-axis sensor (SAS).

In some examples, catheter 21 comprises a braid 76 of wires, which is flexible, disposed along axis 70, and is configured o exchange signals between distal tip 40 and console 24.

In some examples, outer shaft 88 (shown in broken lines in FIG. 3B) is coupled to distal tip 40 and is coaxially disposed around inner shaft 77. Note that the rotation of shaft 22 that is shown in FIG. 3B by rotary direction 72, is referred to outer shaft 88 and not to inner shaft 77.

In some examples, inner shaft 77 is configured to be deflected relative to axis 70, and outer shaft 88 is flexible and is configured to be deflected together with inner shaft 77. In the example of FIG. 3B, distal tip 40 and shaft 22 are shown in two positions: (i) a straight position (without deflection), so that the inner and outer shaft, and distal tip 40 are parallel to axis 70, and (ii) in a deflected position, in which the inner and outer shafts, and distal tip 40 are deflected, at a bending point 82, relative to axis 70. The amount of deflection is shown by a deflection angle 71 between (a) an extension of axis 70 in the straight (non-deflected) position, and (b) an axis 70 a, which represents the longitudinal axis of the deflected portion of shaft 22 and the deflection of distal tip 40. Note that distal tip 40 and shaft 22 can be only at one of the positions at the same time. For example, (i) when moving catheter 21 toward heart 26, distal tip 40 and shaft 22 are typically in the straight position, and (ii) the deflection is typically carried out only when distal tip 40 is positioned within cavity 33 of heart 26, e.g., for performing Intra-Cardiac Echocardiography (ICE) imaging of tissue in question in heart 26. In an example, four-dimensional (4D) ICE provides visualizing operation of an ablation catheter (not shown) within a three-dimensional (3D) space of cavity 33 of heart 26.

In the example of FIG. 3B, the deflection is shown in an XZ plane of the XYZ coordinate system, i.e., below and/or above the location of distal tip 40 (along the Z-axis) in the straight position. In other examples, the deflection may also be carried out in an XY plane (i.e., into and/or out of the plane of the page). In other words, when looking at catheter 21 from a direction 74, axis 70a may appear above, below, to the left or to the right, relative to axis 70.

In some examples, when applying both the deflection (to inner shaft 77) and the rotation (to outer shaft 88) at the same time, 2D array 50 of distal tip 40 may be located at a selected position along a virtual circle about axis 70, as shown in FIG. 4 below.

In yet another alternative example, a catheter within the scope of the present disclosure may have an inverted arrangement relative to the other examples provided herein. More specifically, a catheter may be configured such that it is an outer shaft that controls deflection and an inner shaft that controls rotation. Such an example is described by International Patent Publication No. WO 2018/017717 A1, entitled Medical Devices and Methods of Use, which is incorporated in its entirety herein.

Visualizing Parameters Indicative of the Manipulation of a 4D Ultrasound Catheter FIG. 4 is a schematic, pictorial illustration of frame 31 for presenting on display 27 one or more parameters indicative of the manipulation applied to shaft 22 and distal tip 40, in accordance with an example of the present disclosure. In the context of the present disclosure and in the claims, the term "manipulation" refers to the amount (e.g., angle) of rotation and/or deflection applied to shaft 22 and distal tip 40 as described in detail in FIGS. 2, 3A and 3B above.

In some examples, frame 31 is displayed on display 27 (as shown in FIG. 1 above) and comprises a numeric representation of deflection angle 71 and a rotation angle 73 produced by rotating outer shaft in rotary direction 72.

In some examples, frame 31 comprises a side-view of a virtual conus 80 shown in broken lines, whose (i) origin corresponds to bending point 82 (shown in FIG. 3B above), (ii) central axis corresponds to axis 70 (shown in FIGS. 3A and 3B above), and (iii) a circle 84, corresponds to the maximal deflection angle 71 and rotation angle 73 applied to shaft 22 and distal tip 40. Note that in the present example, the volume within virtual conus 80 is indicative of possible locations of 2D array 50 and the deflected and rotated portion of shaft 22, and the position of 2D array 50.

In some examples, processor 39 is configured to hold a model indicative of the mechanical properties of shaft 22. Processor 39 may use the model for displaying the amount (e.g., angle or angles) of bending and the shape of shaft 22 in response to the first and second position signals received from position sensors 52 and 99. In the present example, shaft 22 is made from any suitable biocompatible material, such as but not limited to titanium, titanium alloy, nickel-titanium alloy also known as nitinol, and based on the model and the position signals received from position sensors 52 and 99, processor 39 is configured to display the shape of shaft 22 and the position of 2D array 50 within the volume of virtual conus 80.

Reference is now made back to FIG. 3B. In case physician 30 rotates (the entire length of) catheter 21 along axis 70, the rotation is sensed by both position sensors 52 and 99. In case physician 30 uses knob 60 for rotating only outer shaft 88 about axis 70, position sensor 52 senses the rotation, but position sensor 99 does not sense any rotation. When shaft 22 is not deflected, the position of 2D array is similar in both rotation cases described above. However, when physician 30 uses knob 66 for deflecting inner shaft 77, the position signals received from both position sensors 52 and 99 are essential for presenting the shape of shaft 22 within virtual conus 80.

In some examples, processor 39 is configured to estimate coordinates in the position tracking system (described in FIG. 1 above) the position and orientation of distal tip 40, at least based on the signal received from position sensor 52. In other words, the position signal received from position sensor 52 is typically sufficient for providing the position and orientation of 2D array in the XYZ coordinate system of system 20. However, in order to estimate and display the deflection and/or rotation angles applied by knobs 66 and 60, respectively, processor 39 must use the position signals from both position sensors 52 and 99.

Reference is now made back to FIG. 4. In some examples, frame 31 comprises a view, from direction 74, of the shape of shaft 22 and the position of 2D array 50, within the volume of virtual conus 80. In this view, circle 84 represents the maximal deflection of shaft 22 relative to axis 70 (e.g., in case inner shaft 88 is rigid and does not bend beyond bending point 82), which is represented by the position of bending point 82 at the center of circle 84.

In some examples, the shape of shaft 22 is also indicative of rotation angle 73, and provides physician 30 with an indication of: (i) the deflection and rotation angles of shaft 22, and (ii) the position of 2D array 50 relative to axis 70 and bending point 82. Note that the view from direction 74 is indicative of how distal tip 40 is "seen" by the tissue intended to be imaged using 2D array 50.

The presentation configuration of FIG. 4 is provided by way of example, in order to provide physician 30 (or any user of system 20) with an indication of the amount (e.g., angles) of rotation and/or deflection applied to shaft 22 and distal tip 40 and/or 2D array 50. This non-limiting example of graphical user interface (GUI) is presented for the sake of conceptual clarity, and the principles described above may be used for designing and displaying any other suitable GUI on display 27.

Figure 5:
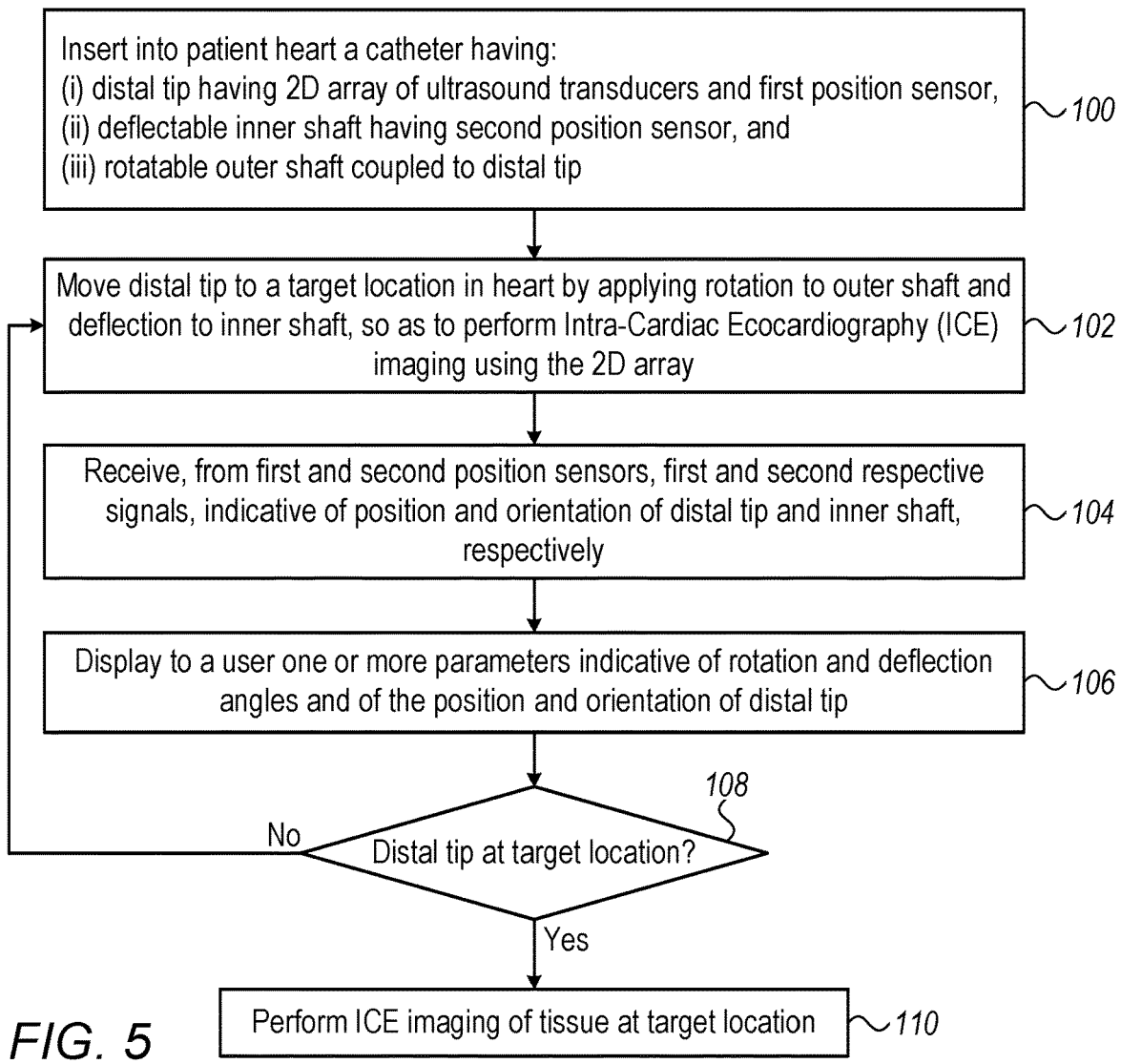
FIG. 5 is a flow chart that schematically illustrates a method for controlling and visualizing manipulation of the catheter in a patient heart, in accordance with an example of the present disclosure.

FIG. 5 is a flow chart that schematically illustrates a method for controlling and visualizing manipulation of distal tip 40 and shaft 23 in heart 26, in accordance with an example of the present disclosure.

The method begins at a catheter insertion step 100, with inserting, into cavity 33 of heart 26, (a) distal tip 40, which has 2D array 50 and position sensor 52, and (b) shaft 22 having: (i) rotatable outer shaft 88 coupled to distal tip 40, and (ii) deflectable inner shaft 77 having position sensor 99, as described in detail in FIGS. 3A and 3B above.

At a distal tip moving step 102, physician 30 uses handle 32 for moving distal tip 40 to a target location in heart 26, so as to perform ICE imaging of tissue at target location using 2D array 50, as described in detail in FIGS. 1, 2, 3A and 3B above.

At a signal receiving step 104, processor 39 receives from position sensors 52 and 99, first and second respective signals, indicative of the position and orientation of distal tip 40 and inner shaft 77, respectively.

At a displaying step 106, processor displays, e.g., on display 27, frame 31 having one or more parameters indicative of rotation angle 73 and deflection angle 71 applied to shaft 22, and the position and orientation of distal tip 40 and/or 2D array 50 in cavity 33 of heart 26, as described in detail in FIGS. 3A, 3B and 4 above. Note that by having indications of the amount (e.g., angles) of deflection and rotation displayed on display 27, physician 30 does not have to check the position of markers 62 and 61 in handle 32, and can dedicates his/her attention in heart 26 and in catheter 21 within heart 26.

At a decision step 108, physician 30 checks whether distal tip 40 is located at the target location. If not, the method loops back to step 102 for adjusting the rotation and or deflection applied to distal tip 40. In case physician 30 identifies that distal tip 40 is positioned at the target location, the method proceeds to an imaging step 110 that concludes the method, in which physician 30 uses 2D array 50 and processor 39 for performing the ICE imaging in the tissue at the target location.

The method of FIG. 5 is intended to improve the quality of performing ICE imaging in heart 26 or in any other suitable organ of patient 28. By having indications of the amount (e.g., angles) of deflection and/or rotation displayed on display 27, physician 30 may focus his/her gaze and attention on heart 26 and distal tip 40, and does not have to waste time and attention on checking the position of markers 62 and 61 in handle 32.

Figure 6:
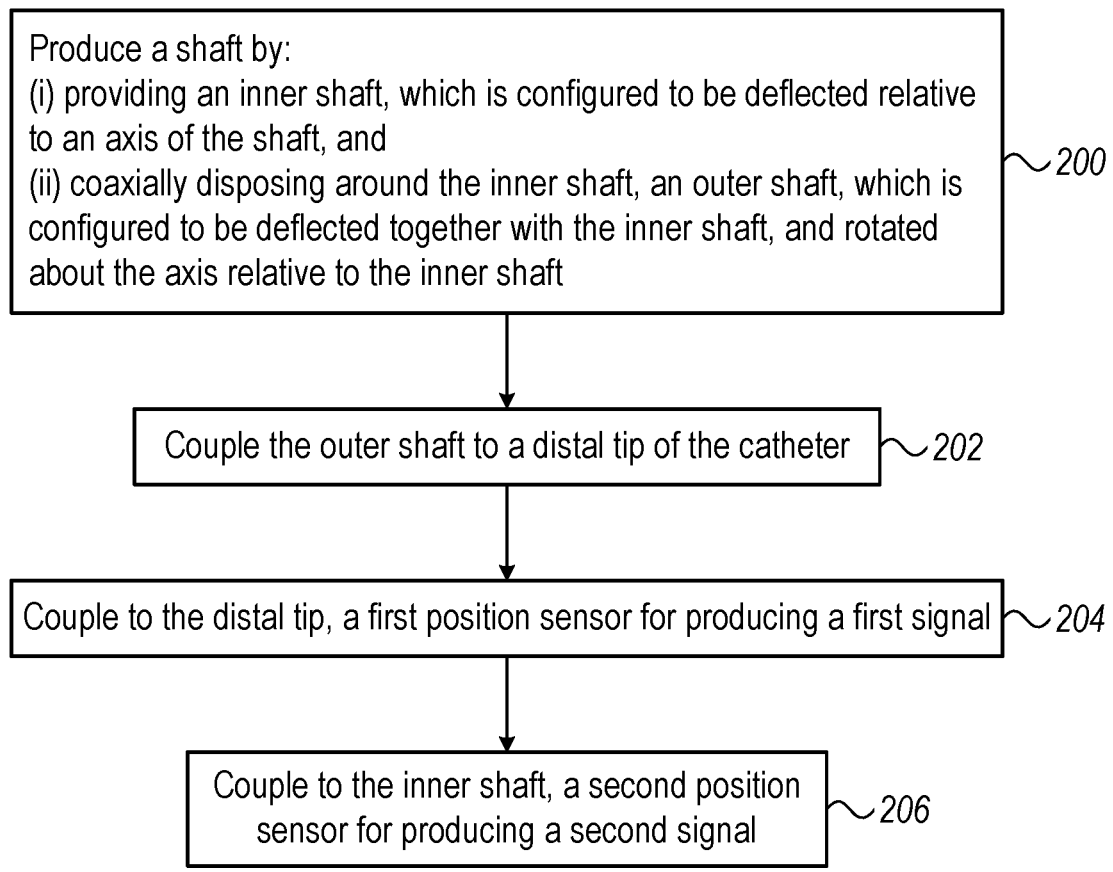
FIG. 6 is a flow chart that schematically illustrates a method for producing a catheter having multiple shafts, in accordance with an example of the present disclosure.

FIG. 6 is a flow chart that schematically illustrates a method for producing catheter 21 having inner shaft 77 and outer shaft 88, in accordance with an example of the present disclosure.

The method begins at a shaft production step 200 with producing shaft 22 by: (i) providing inner shaft 77, which is configured to be deflected relative to axis 70, and (ii) coaxially disposing around inner shaft 77, outer shaft 88, which is configured to be deflected together with inner shaft 77, and rotated about axis 70 relative to inner shaft 77.

At a distal tip coupling step 202, outer shaft 88 is coupled to distal tip 40 using any suitable coupling technique, such as but not limited to Pebax injection molding.

At a first position sensor coupling step 204, position sensor 52, in the present example a dual-axis magnetic-based position sensor produced on a flexible circuit board as described in FIG. 2 above, is coupled to distal tip 40.

At a second position sensor coupling step 206 that concludes the method, position sensor 99, in the present example a DAS or a SAS, is coupled to inner shaft 77.

The method of FIG. 6 is simplified for the sake of conceptual clarity and is provided by way of example. In other examples, the order of the steps may alter for the sake of improved productivity and/or supply chain considerations.

In some examples, the method comprises additional steps, such as but not limited to: (i) threading braid 76 of wires between console 24 and distal tip 40 for exchanging signals therebetween, (ii) connecting the proximal end of wires of braid 76 to console 24, and (iii) integrating handle 32 with catheter 21 for controlling the motion of distal tip 40 and shaft 22.

Example 1

A catheter (21) including a shaft (22) for insertion into an organ (26) of a patient (28), a first position sensor (52) and a second position sensor (99). The shaft (22) includes: (i) an inner shaft (77), which is configured to be deflected relative to an axis (70) of the shaft (22), and (ii) an outer shaft (88), which is coupled to a distal tip (40) of the catheter (21) and is configured to be: (i) coaxially disposed around the inner shaft (77), (ii) deflected together with the inner shaft (77), and (iii) rotated about the axis (70) relative to the inner shaft (77). The first position sensor (52) is coupled to the distal tip (40) and is configured to produce a first signal, and the second position sensor (99) is coupled to the inner shaft (77), and is configured to produce a second signal.

Example 2

The catheter according to Example 1, wherein the first position sensor includes a dual-axis sensor (DAS).

Example 3

The catheter according to Example 2, wherein the DAS is formed on a flexible circuit board (CB).

Example 4

The catheter according to Example 1, wherein the second position sensor includes a dual-axis sensor (DAS) or a single-axis sensor (SAS).

Example 5

The catheter according to Examples 1 through 4, and including a processor, which is configured to estimate, based on at least the first signal, a position and an orientation of the distal tip.

Example 6

The catheter according to Example 5, and including a rotation knob, which is configured to control a rotation of the outer shaft about the axis, and wherein, based on the first and second signals, the processor is configured to display to a user, a parameter indicative of a rotation angle of the rotation.

Example 7

The catheter according to Example 6, wherein the processor is configured to display the parameter using one or both of: a graphic representation, and a numeric representation of the parameter.

Example 8

The catheter according to Example 5, and including a deflection knob, which is configured to control a deflection of the inner shaft relative to the axis, and wherein, based on the first and second signals, the processor is configured to display to a user, a parameter indicative of a deflection angle of the deflection.

Example 9

The catheter according to Examples 1 through 4, and including an ultrasound (US) probe, which is coupled to the distal tip, and is configured to apply US signals to tissue of the organ.

Example 10

The catheter according to Example 9, wherein the organ includes a heart, wherein the US probe includes a two-dimensional (2D) array of ultrasound transducers (UT), and wherein the US probe is configured to perform Intra-Cardiac Echocardiography (ICE) imaging in the heart.

Example 11

A method, including:
(i) inserting into an organ (26) of a patient (28) a catheter (21) including:
  a. an inner shaft (77), which is deflectable relative to an axis (70) of the shaft (22);
  b. an outer shaft (88), which is: (i) coupled to a distal tip (40) of the catheter (21), and is coaxially disposed around the inner shaft (77), and (ii) can be deflected together with the inner shaft (77), and rotated about the axis (70) relative to the inner shaft (77);
  c. a first position sensor (52), coupled to the distal tip (40) for producing a first signal; and
  d. a second position sensor (99), which is coupled to the inner shaft (77) for producing a second signal
(ii) moving the catheter in the organ and receiving the first and second signals; and
(iii) based on the first and second signals, displaying to a user one or more parameters indicative of at least a rotation angle of the distal tip relative to the axis.

Example 12

The method according to Example 11, and including estimating, based on at least the first signal, a position and an orientation of the distal tip.

Example 13

The method according to Example 12, wherein moving the catheter includes one or both of rotating the outer shaft about the axis, and deflecting the inner shaft relative to the axis, and wherein displaying the one or more parameters includes, displaying a parameter indicative of a deflection angle of the distal tip relative to the axis.

Example 14

The method according to Example 13, wherein displaying the one or more parameters includes displaying one or both of a graphic representation, and a numeric representation of the one or more parameters.

Example 15

The method according to Examples 11 through 14, and including applying ultrasound (US) signals to tissue of the organ.

Example 16

The method according to Example 15, wherein the organ includes a heart, and wherein applying the US signals includes performing Intra-Cardiac Echocardiography (ICE) imaging in the heart.

Example 17

A method for producing a catheter (21), the method including:
(i) producing a shaft (22) by:
  a. providing an inner shaft (77), which is configured to be deflected relative to an axis (70) of the shaft (22);
  b. coaxially disposing around the inner shaft (77), an outer shaft (88), which is configured to be deflected together with the inner shaft (77), and rotated about the axis (70) relative to the inner shaft (77), and coupling the outer shaft (88) to a distal tip (40) of the catheter (21);
(ii) coupling to the distal tip (40), a first position sensor (52) for producing a first signal; and
(iii) coupling to the inner shaft (77), a second position sensor (99) for producing a second signal.

Example 18

The method according to Example 17, wherein coupling the first position sensor includes coupling a dual-axis sensor (DAS).

Example 19

The method according to Example 18, wherein the DAS is formed on a flexible circuit board (CB).

Example 20

The method according to Example 17, wherein coupling the second position sensor includes coupling a dual-axis sensor (DAS) or a single-axis sensor (SAS).

Although the examples described herein mainly address 4D US imaging of a patient heart, the methods and systems described herein can also be used in other patient organs in in other applications.

It will thus be appreciated that the examples described above are cited by way of example, and that the present disclosure is not limited to what has been particularly shown and described hereinabove. Rather, the scope of the present disclosure includes both combinations and sub-combinations of the various features described hereinabove, as well as variations and modifications thereof which would occur to persons skilled in the art upon reading the foregoing description and which are not disclosed in the prior art.

The invention claimed is:

1. A system comprising: a catheter; and a display, wherein the catheter comprises:
   a shaft for insertion into an organ of a patient, the shaft comprising:
   an inner shaft, which is configured to be deflected relative to an axis of the shaft; and
   an outer shaft, which is coupled to a distal tip of the catheter and is configured to be: (i) coaxially disposed around the inner shaft, (ii) deflected together with the inner shaft, and (iii) rotated about the axis relative to the inner shaft;
   a first position sensor, which is coupled to the distal tip and is configured to produce a first signal; and
   a second position sensor, which is coupled to the inner shaft, and is configured to produce a second signal,
   wherein the display is configured to use the first and second signals to display to a user one or more parameters indicative of at least a rotation angle of the distal tip relative to the axis, wherein displaying the one or more parameters comprises displaying a cone, wherein an origin of the cone corresponds to a bending point, wherein a central axis of the cone corresponds to the axis of the shaft, and a circle of the cone is determined, at least in part, by the rotation angle.

2. The catheter according to claim 1, wherein the first position sensor comprises a dual-axis sensor (DAS).

3. The catheter according to claim 2, wherein the DAS is formed on a flexible circuit board (CB).

4. The catheter according to claim 1, wherein the second position sensor comprises a dual-axis sensor (DAS) or a single-axis sensor (SAS).

5. The catheter according to claim 1, and comprising a processor, which is configured to estimate, based on at least the first signal, a position and an orientation of the distal tip.

6. The catheter according to claim 5, and comprising a rotation knob, which is configured to control a rotation of the outer shaft about the axis, and wherein, based on the first and second signals, the processor is configured to display to a user, a parameter indicative of a rotation angle of the rotation.

7. The catheter according to claim 6, wherein the processor is configured to display the parameter using one or both of: a graphic representation, and a numeric representation of the parameter.

8. The catheter according to claim 5, and comprising a deflection knob, which is configured to control a deflection of the inner shaft relative to the axis, and wherein, based on the first and second signals, the processor is configured to display to a user, a parameter indicative of a deflection angle of the deflection.

9. The catheter according to claim 1, and comprising an ultrasound (US) probe, which is coupled to the distal tip, and is configured to apply US signals to tissue of the organ.

10. The catheter according to claim 9, wherein the organ comprises a heart, wherein the US probe comprises a two-dimensional (2D) array of ultrasound transducers (UT), and wherein the US probe is configured to perform Intra-Cardiac Ecocardiography (ICE) imaging in the heart.

11. A method, comprising:
   inserting into an organ of a patient a catheter comprising:
   a shaft comprising:
   an inner shaft, which is deflectable relative to an axis of the shaft;
   an outer shaft, which is: (i) coupled to a distal tip of the catheter, and is coaxially disposed around the inner shaft, and (ii) can be deflected together with the inner shaft, and rotated about the axis relative to the inner shaft;
   a first position sensor, coupled to the distal tip for producing a first signal; and
   a second position sensor, which is coupled to the inner shaft for producing a second signal;
   moving the catheter in the organ and receiving the first and second signals, wherein moving the catheter comprises one or both of rotating the outer shaft about the axis or deflecting the inner shaft relative to the axis;
   estimating, based on at least the first signal, a position and an orientation of the distal tip; and
   based on the first and second signals, displaying to a user one or more parameters indicative of at least a rotation angle of the distal tip relative to the axis, wherein displaying the one or more parameters comprises displaying a cone, wherein an origin of the cone corresponds to a bending point, wherein a central axis of the cone corresponds to the axis of the shaft, and a circle of the cone is determined, at least in part, by the rotation angle.

12. The method according to claim 11, wherein displaying the one or more parameters comprises displaying one or both of a graphic representation, and a numeric representation of the one or more parameters.

13. The method according to claim 11, and comprising applying ultrasound (US) signals to tissue of the organ.

14. The method according to claim 13, wherein the organ comprises a heart, and wherein applying the US signals comprises performing Intra-Cardiac Echocardiography (ICE) imaging in the heart.

15. The method according to claim 11, wherein the first position sensor is disposed distal relative to the bending point and wherein the second position sensor is disposed proximal relative to the bending point.

16. The method according to claim 11, wherein the first position sensor is configured to sense rotation of the outer shaft and wherein the second position sensor is not configured to sense rotation of the outer shaft.

17. A method for producing and using a catheter, the method comprising:
   producing a shaft by:
   providing an inner shaft, which is configured to be deflected relative to an axis of the shaft;
   coaxially disposing around the inner shaft, an outer shaft, which is configured to be deflected together with the inner shaft, and rotated about the axis relative to the inner shaft, and coupling the outer shaft to a distal tip of the catheter;

coupling to the distal tip, a first position sensor for producing a first signal; and coupling to the inner shaft, a second position sensor for producing a second signal, based on the first and second signals, displaying to a user one or more parameters indicative of at least a rotation angle of the distal tip relative to the axis, wherein displaying the one or more parameters comprises displaying a cone, wherein an origin of the cone corresponds to a bending point, wherein a central axis of the cone corresponds to the axis of the shaft, and a circle of the cone is determined, at least in part, by the rotation angle.

18. The method according to claim 17, wherein coupling the first position sensor comprises coupling a dual-axis sensor (DAS).

19. The method according to claim 18, wherein the DAS is formed on a flexible circuit board (CB).

20. The method according to claim 17, wherein coupling the second position sensor comprises coupling a dual-axis sensor (DAS) or a single-axis sensor (SAS).

21. A system comprising: a catheter; and a display, wherein the catheter comprises:

a shaft for insertion into an organ of a patient, the shaft comprising:

an outer shaft, which is configured to be deflected relative to an axis of the shaft; and an inner shaft, which is coupled to a distal tip of the catheter and is configured to be: (i) coaxially disposed around the inner shaft, (ii) deflected together with the inner shaft, and (iii) rotated about the axis relative to the outer shaft;

a first position sensor, which is coupled to the distal tip and is configured to produce a first signal; and a second position sensor, which is coupled to the outer shaft, and is configured to produce a second signal, wherein the display is configured to use the first and second signals to display to a user one or more parameters indicative of at least a rotation angle of the distal tip relative to the axis, wherein displaying the one or more parameters comprises displaying a cone, wherein an origin of the cone corresponds to a bending point, wherein a central axis of the cone corresponds to the axis of the shaft, and a circle of the cone is determined, at least in part, by the rotation angle.

* * * * *